United States Patent
Yagyu (10) Patent No.: US 12,154,781 B2
(45) Date of Patent: Nov. 26, 2024

(54) ULTRAVIOLET IRRADIATION DEVICE USING EXCIMER LAMPS

(71) Applicant: Ushio Denki Kabushiki Kaisha, Tokyo (JP)

(72) Inventor: Hideaki Yagyu, Tokyo (JP)

(73) Assignee: Ushio Denki Kabushiki Kaisha, Tokyo (JP)

( * ) Notice: Subject to any disclaimer, the term of this patent is extended or adjusted under 35 U.S.C. 154(b) by 406 days.

(21) Appl. No.: 17/619,927

(22) PCT Filed: Aug. 5, 2020

(86) PCT No.: PCT/JP2020/030005
§ 371 (c)(1),
(2) Date: Dec. 16, 2021

(87) PCT Pub. No.: WO2021/025063
PCT Pub. Date: Feb. 11, 2021

(65) Prior Publication Data
US 2022/0359186 A1 Nov. 10, 2022

(30) Foreign Application Priority Data

Aug. 5, 2019 (JP) .................. 2019-143960
Aug. 7, 2019 (JP) .................. 2019-145557

(51) Int. Cl.
*H01J 61/54* (2006.01)
*A61L 2/10* (2006.01)
(Continued)

(52) U.S. Cl.
CPC ............... *H01J 61/54* (2013.01); *A61L 2/10* (2013.01); *H01J 61/16* (2013.01); *H01J 61/40* (2013.01); *A61L 2202/11* (2013.01)

(58) Field of Classification Search
CPC .................................. A61L 2/0047
See application file for complete search history.

(56) References Cited

U.S. PATENT DOCUMENTS 6,084,360 A 7/2000 Yokokawa et al.
2006/0097657 A1* 5/2006 Kogure ............. H05B 41/2806
 315/248
(Continued)

FOREIGN PATENT DOCUMENTS

CN 1713337 A 12/2005
JP H08-153493 A 6/1996
(Continued)

OTHER PUBLICATIONS

An Office Action mailed by China National Intellectual Property Administration on Sep. 14, 2023, which corresponds to Chinese Patent Application No. 202080004491.0 and is related to U.S. Appl. No. 17/619,927; with English language translation.
(Continued)

*Primary Examiner* — Andrew Smyth
(74) *Attorney, Agent, or Firm* — Studebaker & Brackett PC (57) ABSTRACT

Provided is an ultraviolet irradiation device including an excimer lamp, a main emission wavelength of which belongs to a wavelength band of 190-230 nm (first wavelength band), the ultraviolet irradiation device that shows high startability. This ultraviolet irradiation device includes: a lamp house on at least one surface of which a light extraction surface is formed; an excimer lamp accommodated in the lamp house, the excimer lamp that emits ultraviolet light, a main emission wavelength of which belongs to a first wavelength band of 190-230 nm; and a start assist light source arranged in a position in which ultraviolet (Continued)

light, a main emission wavelength of which belongs to a second wavelength band of 250-300 nm, is capable of being irradiated to the excimer lamp.

12 Claims, 7 Drawing Sheets (51) Int. Cl.
  *H01J 61/16* (2006.01)
  *H01J 61/40* (2006.01)

(56) References Cited

U.S. PATENT DOCUMENTS

| 2006/0139934 | A1 | 6/2006 | Hirohashi et al. |
| 2006/0164830 | A1 | 7/2006 | Justel |
| 2020/0234941 | A1* | 7/2020 | Yagyu ............... H01J 61/025 |

FOREIGN PATENT DOCUMENTS

| JP | H10-223384 A | 8/1998 | |
| JP | 2002-279820 A | 9/2002 | |
| JP | 2006-040867 A | 2/2006 | |
| JP | 2017-068944 A | 4/2017 | |
| JP | 2018-055965 A | 4/2018 | |
| JP | 2018-200744 A | 12/2018 | |
| KR | 2001-0066924 A | 7/2001 | |
| WO | WO-2018131582 A1 * | 7/2018 | ........... A61L 2/0047 |

OTHER PUBLICATIONS

Notification of Transmittal of Translation of the International Preliminary Report on Patentability and Translation of Written Opinion of the International Searching Authority; PCT/JP2020/030005; mailed on Feb. 17, 2022.

The partial supplementary European search report (R. 164 EPC)) issued by the European Patent Office on Sep. 9, 2022, which corresponds to European Patent Application No. 20849856.8-1212 and is related to U.S. Appl. No. 17/619,927.

The partial supplementary European search report (R. 164 EPC)) issued by the European Patent Office on Sep. 9, 2022, which corresponds to European Patent Application No. 20849436.9-1212 and is related to U.S. Appl. No. 17/619,927.

International Search Report issued in PCT/JP2020/030005; mailed Oct. 13, 2020.

* cited by examiner

ULTRAVIOLET IRRADIATION DEVICE USING EXCIMER LAMPS

TECHNICAL FIELD

The present invention relates to an ultraviolet irradiation device, and especially relates to an ultraviolet irradiation device including an excimer lamp.

BACKGROUND ART

Conventionally, an excimer lamp has a problem of a large-size power source for lighting because a high voltage is required when starting lighting in a low temperature state or a dark state, or after a long dormant state. In contrast, Patent Document 1 below proposes an ultraviolet irradiation device provided with a UV-LED that radiates ultraviolet light of 390 nm as a start assist light source, the device that irradiates an excimer lamp with light emitted from the UV-LED to assist start-up.

Patent Document 1 discloses an excimer lamp of an emission wavelength of 172 nm that uses a Xe gas as a luminescent gas (discharge gas) as an embodiment. Furthermore, Patent Document 1 simply lists various materials in addition to Xe as the luminescent gas (discharge gas) that may be used as the excimer lamp. Specifically, as a combination of the luminescent gas and emission wavelength, it is listed as Ar gas with 126 nm, Kr gas with 146 nm, ArBr gas with 165 nm, ArF gas with 193 nm, KrCl gas with 222 nm, XeI gas with 253 nm, XeCl gas with 308 nm, XeBr gas with 283 nm, and KrBr gas with 207 nm.

PRIOR ART DOCUMENT

Patent Document

Patent Document 1: JP-A-2017-68944

SUMMARY OF THE INVENTION

Problems to be Solved by the Invention

Ultraviolet light, a main emission wavelength of which is in a wavelength band of 190-230 nm (hereinafter referred to as a "first wavelength band") is absorbed by the stratum corneum of the skin and does not travel to an inner side (basal stratum side) even if this is irradiated to the human skin. Since corneocytes contained in the stratum corneum are dead cells, there is hardly any risk that the ultraviolet light is absorbed by living cells such as the stratum *spinosum*, stratum *granulosum*, and dermis to damage DNA as in a case where ultraviolet light of a wavelength of 254 nm is irradiated, for example.

Furthermore, it is known that the ultraviolet light in this first wavelength band has a sterilization effect on an irradiation target. Therefore, it is expected that an ultraviolet irradiation device equipped with an excimer lamp that emits the ultraviolet light in the first wavelength band is utilized for various applications including photosterilization activity.

However, as a result of earnest studies by the present inventor, it has been found that startability of the excimer lamp that emits the ultraviolet light belonging to the first wavelength band is not so excellent.

As described above, Patent Document 1 also discloses the excimer lamp that emits the ultraviolet light of the wavelength belonging to the first wavelength band in addition to the Xe excimer lamp of 172 nm. However, according to the studies of the present inventor, an excimer lamp the main emission wavelength of which is 222 nm in which a KrCl gas is sealed (hereinafter referred to as a "KrCl excimer lamp") did not light at all with ultraviolet light of 390 nm.

In view of the above-described problem, an object of the present invention is to provide an ultraviolet irradiation device including an excimer lamp, a main emission wavelength of which belongs to a wavelength band of 190-230 nm (first wavelength band), the ultraviolet irradiation device that shows high startability.

Means for Solving the Problems

An ultraviolet irradiation device according to the present invention is provided with:
- a lamp house on at least one surface of which a light extraction surface is formed;
- an excimer lamp accommodated in the lamp house, the excimer lamp that emits ultraviolet light, a main emission wavelength of which belongs to a first wavelength band of 190-230 nm; and
- a start assist light source arranged in a position in which ultraviolet light, a main emission wavelength of which belongs to a second wavelength band of 250-300 nm, is capable of being irradiated to the excimer lamp.

In this specification, the "main emission wavelength" indicates a wavelength $\lambda i$ in a wavelength range $Z(\lambda i)$ showing integrated intensity of 40% or larger with respect to the total integrated intensity in an emission spectrum in a case where a wavelength range $Z(\lambda)$ of $\pm 10$ nm with respect to a certain wavelength $\lambda$ is defined on the emission spectrum. For example, in a light source having an extremely narrow half-value width and showing light intensity only at a specific wavelength such as an excimer lamp in which a luminescent gas containing KrCl, KrBr, and ArF is sealed, a wavelength having the highest relative intensity (main peak wavelength) may be usually made the main emission wavelength.

As a result of the earnest studies, the present inventor found that the KrCl excimer lamp does not light even after standby time for one minute or longer in a case where a UV-LED of 365 nm is used as a start assist light source of the KrCl excimer lamp. Furthermore, as a result of the earnest studies, the present inventor found that the KrCl excimer lamp lights immediately (in one second) in a case where a UV-LED of 280 nm is used as the start assist light source of the KrCl excimer lamp.

In a case of the excimer lamp that emits the ultraviolet light, the main emission wavelength of which is in the wavelength band of 190-230 nm (first wavelength band), halogen gases such as Cl, Br, and F are contained as the luminescent gas. Since halogen has high electronegativity, this has a high electron adhesive property. Therefore, it is considered that the halogen adheres electrons required for discharge, so that the discharge is less likely to start than that with the Xe excimer lamp.

As described above, energy of the ultraviolet light is higher as the wavelength is shorter. Therefore, it is expected that startability of the excimer lamp is improved by irradiating the excimer lamp, the main emission wavelength of which belongs to the first wavelength band, with ultraviolet light of a wavelength shorter than 365 nm. According to the earnest studies of the present inventor, it has been found that the startability of the excimer lamp is improved by using the ultraviolet light, the main emission wavelength of which belongs to the second wavelength band of 250-300 nm, to assist the start-up of the excimer lamp. A more detailed reason is described later in [MODE FOR CARRYING OUT THE INVENTION].

That is, according to the ultraviolet irradiation device having the above-described configuration, it becomes possible to improve the startability even in a case where the ultraviolet irradiation device includes the excimer lamp that emits the ultraviolet light, the main emission wavelength of which belongs to the first wavelength band of 190-230 nm.

The ultraviolet irradiation device may be provided with a first optical filter that substantially transmits the ultraviolet light in the first wavelength band and substantially reflects the ultraviolet light in the second wavelength band, the optical filter being arranged in the lamp house at a place that the ultraviolet light radiated from the excimer lamp passes through.

In this specification, the description that the optical filter "substantially transmits the ultraviolet light" is intended to mean that intensity of the ultraviolet light transmitted through the optical filter is 60% or larger of the intensity of the ultraviolet light incident on the optical filter. Furthermore, in this specification, the description "substantially reflects the ultraviolet light" is intended to mean that the intensity of the ultraviolet light reflected by the optical filter is 80% or larger of the intensity of the ultraviolet light incident on the optical filter.

Note that transmittance and reflectance of the ultraviolet light of the optical filter actually change according to an incident angle of the ultraviolet light incident on the optical filter. The ultraviolet light emitted from the excimer lamp and the start assist light source travel at a certain divergence angle; among all the traveling light rays, intensity of the light ray traveling at an angle in the vicinity of 0° with respect to a light emission surface is the strongest, and the intensity decreases as the divergence angle is farther from 0°. Therefore, the optical filter having the transmittance of 60% or larger with respect to the intensity of the ultraviolet light incident on the optical filer at the incident angle of 20° or smaller may be treated as the filter that substantially transmits the ultraviolet light. Similarly, the optical filter having the reflectance of 90% or larger with respect to the intensity of the ultraviolet light incident on the optical filer at the incident angle of 30° or smaller may be treated as the filter that substantially reflects the ultraviolet light.

The ultraviolet light, the main emission wavelength of which belongs to the second wavelength band of 250-300 nm, might have some influence on a human body unlike the ultraviolet light, the main emission wavelength of which belongs to the first wavelength band of 190-230 nm. Therefore, for example, at time of day in which a human being is present in the same space and the like, it is not preferable to directly radiate the ultraviolet light in the second wavelength band out of the ultraviolet irradiation device together with the ultraviolet light in the first wavelength band.

In contrast, according to the above-described ultraviolet irradiation device, the first optical filter that substantially transmits the ultraviolet light in the first wavelength band emitted from the excimer lamp but substantially reflects the ultraviolet light in the second wavelength band emitted from the start assist light source is arranged in a place in the lamp house where the ultraviolet light radiated from the excimer lamp passes. As a result, the ultraviolet light in the second wavelength band emitted for assisting the start-up is reflected in the lamp house, so that this is applied to the excimer lamp to achieve a start assist function and is less likely to be radiated out of the ultraviolet irradiation device. In contrast, the ultraviolet light in the first wavelength band assumed to be radiated out of the ultraviolet irradiation device may be reliably extracted from the device.

The first optical filter may be arranged on the light extraction surface of the lamp house.

A luminescent gas containing KrCl or KrBr may be sealed in the excimer lamp.

In a case where the luminescent gas containing KrCl is sealed in the excimer lamp, the main emission wavelength of the ultraviolet light emitted from the excimer lamp is in the vicinity of 222 nm, and in a case where the luminescent gas containing KrBr is sealed in the excimer lamp, the main emission wavelength of the ultraviolet light emitted from the excimer lamp is in the vicinity of 207 nm. Since the ultraviolet light in these wavelength bands shows a high sterilization performance, the ultraviolet irradiation device especially suitable for sterilization applications is achieved.

The start assist light source may be an LED light source including a light emission surface that emits the ultraviolet light in the second wavelength band.

In the above-described configuration,
the excimer lamp may include a pair of electrodes formed on an outer wall of a tube body forming the excimer lamp and arranged apart from each other in a tube axis direction of the tube body,
the start assist light source may include a second optical filter arranged on the light emission surface that substantially transmits the ultraviolet light in the second wavelength band and substantially inhibits the ultraviolet light in the first wavelength band from being irradiated to the start assist light source, and
the start assist light source may be arranged in a position between the pair of electrodes in the tube axis direction as seen in a direction orthogonal to the light extraction surface.

In a case where the excimer lamp has a configuration including the pair of electrodes separated from each other in the tube axis direction, a region interposed between the pair of electrodes mainly forms a light emitting space. Therefore, by arranging the start assist light source in a position between the pair of electrodes in the tube axis direction as seen in the direction orthogonal to the light extraction surface, it becomes possible to irradiate the light emitting space with the ultraviolet light in the second wavelength band at high intensity from the start assist light source. As a result, high startability of the excimer lamp may be obtained.

In contrast, in a case where the start assist light source is arranged in the above-described position, a part of the ultraviolet light in the first wavelength band emitted from the excimer lamp after lighting might be irradiated to the start assist light source side. Especially, in a case where the start assist light source is the LED light source, an LED element is generally sealed with resin and the like, so that the sealing resin may deteriorate over time due to exposure to the ultraviolet light in the first wavelength band.

However, according to the above-described configuration, since the start assist light source includes the second optical filter arranged on the light emission surface that substantially transmits the ultraviolet light in the second wavelength band and substantially inhibits the ultraviolet light in the first wavelength band from being irradiated to the start assist light source, even when the ultraviolet light in the first wavelength band emitted from the excimer lamp after lighting travels to the start assist light source side, this ultraviolet light is returned to the excimer lamp side. As a result, progress in deterioration of the start assist light source formed of the LED light source is suppressed.

Note that, such second optical filter may, for example, have a function of substantially transmitting the ultraviolet light in the second wavelength band but substantially reflecting the ultraviolet light in the first wavelength band. Furthermore, as another example, the second optical filter may have a function of substantially transmitting the ultraviolet light in the second wavelength band but substantially absorbing the ultraviolet light in the first wavelength band.

As another aspect of the ultraviolet irradiation device,
the excimer lamp may include a pair of electrodes formed on an outer wall of a tube body forming the excimer lamp and arranged apart from each other in a tube axis direction of the tube body, and
the start assist light source may be arranged in a position outside the pair of electrodes in the tube axis direction as seen in a direction orthogonal to the light extraction surface.

According to such configuration, the ultraviolet light in the first wavelength band emitted from the excimer lamp after lighting is less likely to be irradiated to the start assist light source. Therefore, even in a case where the start assist light source is formed of the LED light source, the start assist light source is less likely to be deteriorated over time.

The lamp house may be such that an inner wall of at least one surface other than the light extraction surface is formed of a material that substantially reflects the ultraviolet light in the second wavelength band.

According to such configuration, a part of the ultraviolet light in the second wavelength band emitted from the start assist light source may be reflected by the inner wall surface of the lamp house and guided to the light emitting space of the excimer lamp. As a result, the startability of the excimer lamp may be further improved.

The ultraviolet irradiation device may be provided with a light transmissive window provided on a part of a wall surface of the lamp house, in which
the start assist light source may be arranged so as to be fixed to the wall surface of the lamp house outside the lamp house in a state in which the light emission surface faces the light transmissive window.

Note that the start assist light source may be formed of a low-pressure mercury lamp that emits the ultraviolet light in the second wavelength band. Since the low-pressure mercury lamp is extremely excellent in startability as compared with the excimer lamp, this may be used as the start assist light source of the excimer lamp.

Effect of the Invention

According to the present invention, it is possible to achieve an ultraviolet irradiation device with high startability regardless of inclusion of an excimer lamp, a main emission wavelength of which belongs to a wavelength band of 190-230 nm (first wavelength band).

MODE FOR CARRYING OUT THE INVENTION

Each embodiment of an ultraviolet irradiation device according to the present invention is described with reference to the drawings as appropriate. Note that the following drawings are schematically illustrated, and a dimensional ratio on the drawing and an actual dimensional ratio do not always the same. Furthermore, the dimensional ratios do not always the same between the drawings.

First Embodiment

A first embodiment of an ultraviolet irradiation device according to the present invention is described.

Figure 1:
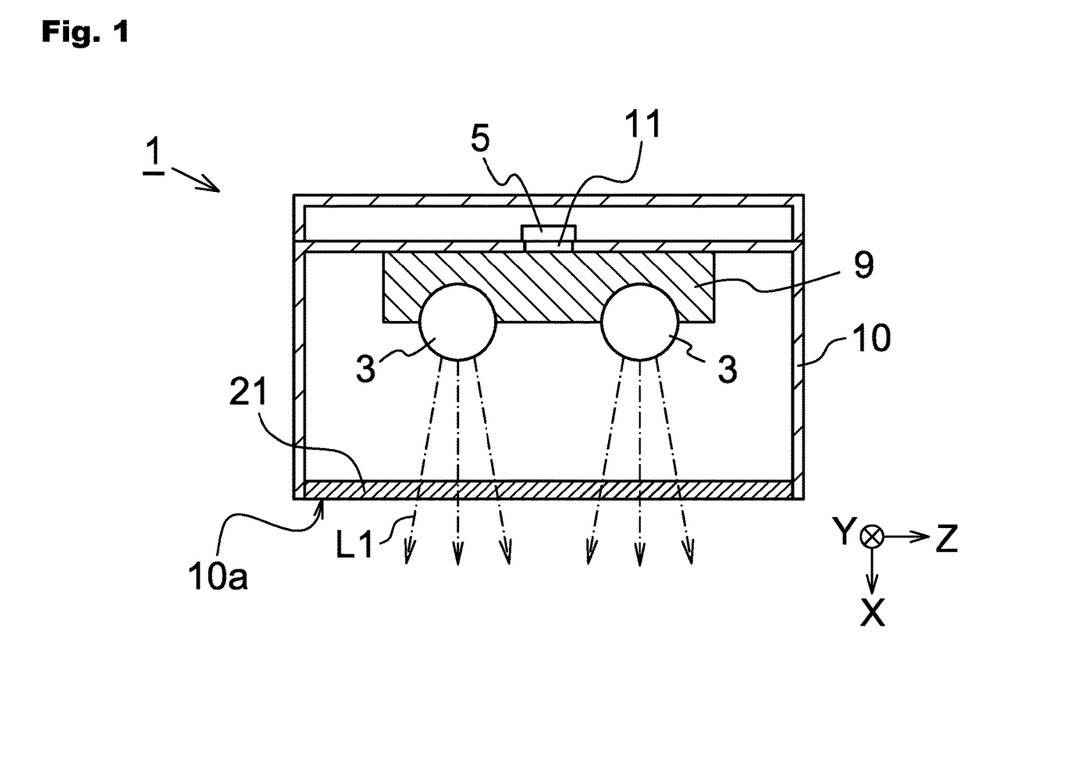
FIG. 1 is a cross-sectional view schematically illustrating a configuration of a first embodiment of an ultraviolet irradiation device of the present invention.

FIG. 1 is a cross-sectional view schematically illustrating an example of a configuration of the ultraviolet irradiation device of this embodiment. As illustrated in FIG. 1, an ultraviolet irradiation device 1 is provided with a lamp house 10 and an excimer lamp 3 accommodated in the lamp house 10. Note that a case where the ultraviolet irradiation device 1 is provided with two excimer lamps (3 and 3) is hereinafter described as an example, but the number of excimer lamps 3 provided on the ultraviolet irradiation device 1 is not limited to two, and may be one or three or larger.

In this embodiment, the lamp house 10 has a substantially rectangular parallelepiped shape, and includes a hollow space so that the excimer lamp 3 and the like may be accommodated therein. Then, one surface 10a of the lamp house 10 forms a light extraction surface for extracting ultraviolet light L1 emitted from the excimer lamp 3 out of the lamp house 10. A first optical filter 21 is formed on this surface 10a (hereinafter, referred to as a "light extraction surface 10a"). A characteristic of the first optical filter 21 is described later.

In the following description, an XYZ coordinate system in which a direction in which the ultraviolet light L1 is extracted from the lamp house 10 is an X direction and a plane orthogonal to the X direction is a YZ plane is appropriately referred to. Note that, in this embodiment, a case where the two excimer lamps (3 and 3), a tube axis direction of which is in a Y direction, are arranged apart from each other in a Z direction is described as an example.

Figure 2:
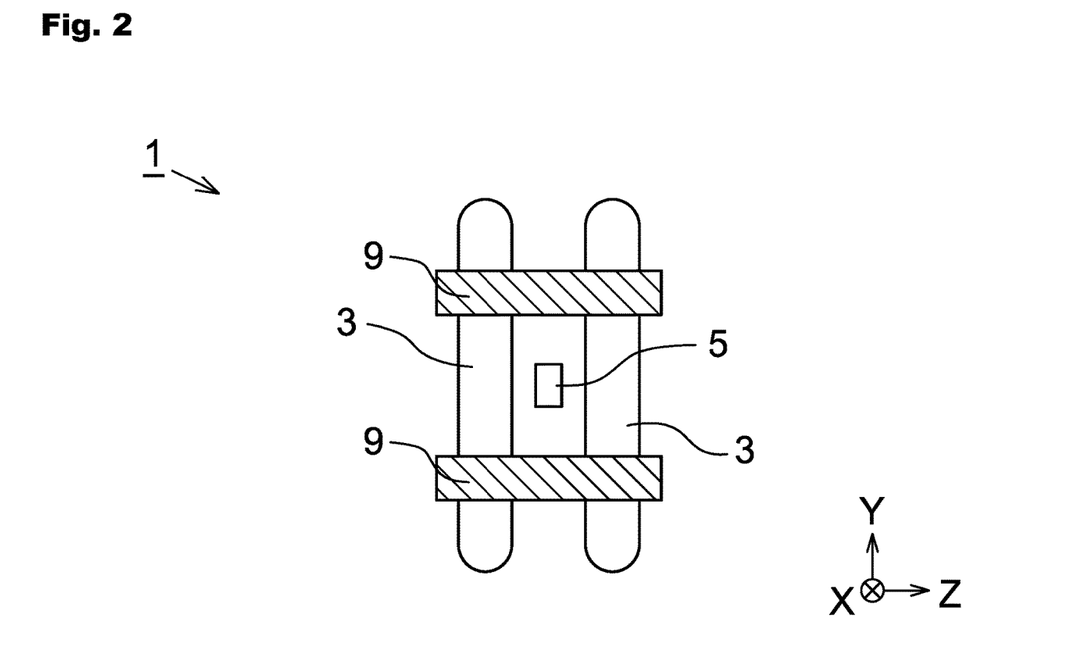
FIG. 2 is a schematic plan view of excimer lamps illustrated in FIG. 1 as seen in an X direction.

FIG. 2 is a schematic plan view of the excimer lamps 3 as seen in the X direction. A pair of electrodes (9 and 9) separated from each other in the Y direction are formed on an outer wall of each excimer lamp 3, the tube axis direction of which is in the Y direction. In FIG. 1, only one electrode 9 of the pair of electrodes (9 and 9) is illustrated.

The ultraviolet irradiation device 1 is provided with a start assist light source 5. In this embodiment, the start assist light source 5 is an LED light source and emits ultraviolet light L2 (refer to FIG. 6), a main emission wavelength of which belongs to a second wavelength band of 250-300 nm. As an example, the start assist light source 5 is the LED light source a peak wavelength of which is 280 nm. In this embodiment, the start assist light source 5 is on an outer side of the lamp house 10 and is fixed to an outer wall of the lamp house 10. On the lamp house 10, a light transmissive window 11 is formed in a position facing a light emission surface of the start assist light source 5. The ultraviolet light L2 emitted from the start assist light source 5 enters the lamp house 10 through the light transmissive window 11. The light transmissive window 11 may be formed of a material film that transmits the ultraviolet light L2, or may be a simple opening.

Figure 3:
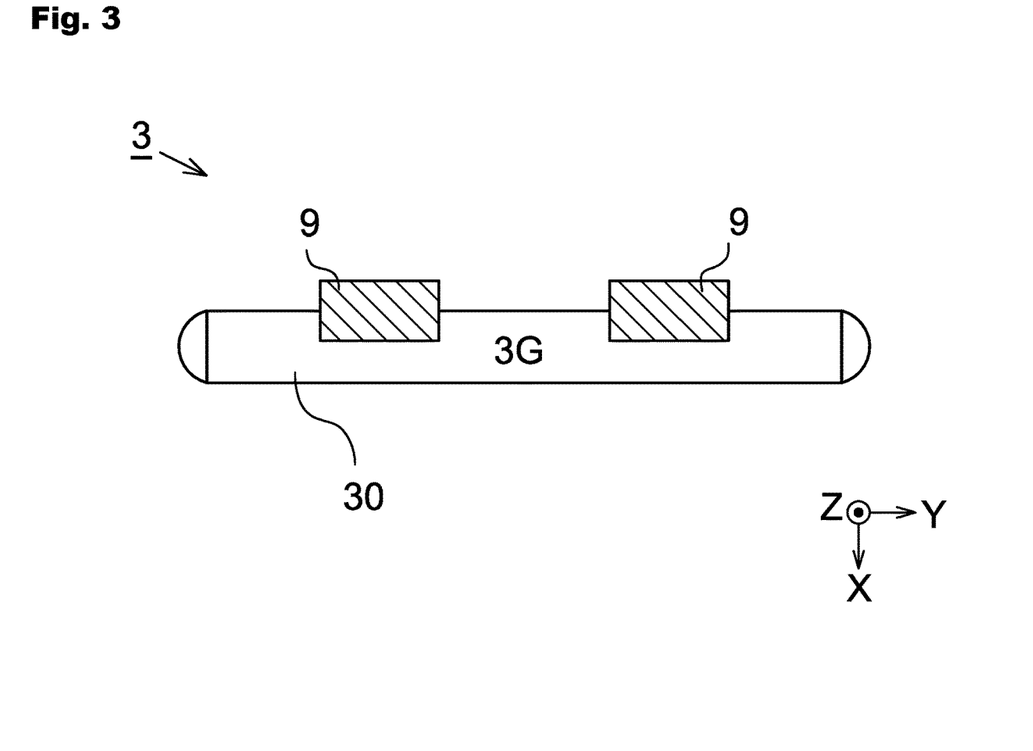
FIG. 3 is a schematic plan view of one excimer lamp illustrated in FIG. 1 as seen in a Z direction.

FIG. 3 is a view schematically illustrating a positional relationship between the excimer lamp 3 and the electrodes (9 and 9) and corresponds to a schematic plan view of the excimer lamp 3 as seen in the Z direction.

As described above, the excimer lamp 3 includes a tube body 30, the tube axis direction of which is in the Y direction. The pair of electrodes (9 and 9) are in contact with an outer wall surface of the tube body 30 in positions separated from each other in the Y direction. A luminescent gas 3G is sealed in the tube body 30. When a high-frequency AC voltage of, for example, about 10 kHz to 5 MHz is applied between the pair of electrodes (9 and 9), the voltage is applied to the luminescent gas 3G via the tube body 30. At that time, discharge plasma is generated in a discharge space in which the luminescent gas 3G is sealed, an atom of the luminescent gas 3G is excited to enter an excimer state, and excimer light emission is generated when this atom shifts to a ground state.

The luminescent gas 3G is made of a material that emits the ultraviolet light L1, the main emission wavelength of which belongs to the first wavelength band of 190-230 nm, at the time of excimer light emission. As an example, the luminescent gas 3G contains KrCl, KrBr, and ArF. Note that, in addition to the above-described gas types, an inert gas such as argon (Ar) or neon (Ne) may also be mixed.

Figure 4:
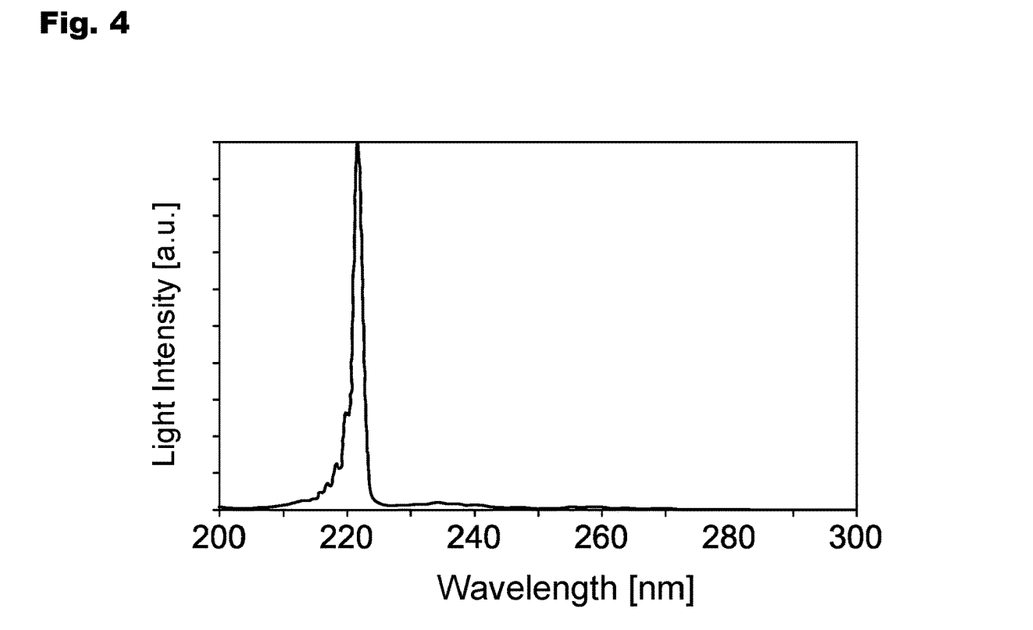
FIG. 4 is an example of a spectrum of ultraviolet light L1 emitted from the excimer lamp in a case in which a luminescent gas contains KrCl.

For example, in a case where the luminescent gas 3G contains KrCl, the excimer lamp 3 emits the ultraviolet light L1, the main emission wavelength of which is in the vicinity of 222 nm. In a case where the luminescent gas 3G contains KrBr, the excimer lamp 3 emits the ultraviolet light L1, the main emission wavelength of which is in the vicinity of 207 nm. In a case where the luminescent gas 3G contains ArF, the excimer lamp 3 emits the ultraviolet light L1, the main emission wavelength of which is in the vicinity of 193 nm. FIG. 4 is an example of a spectrum of the ultraviolet light L1 emitted from the excimer lamp 3 in which the luminescent gas 3G contains KrCl.

In a case where the above-described gas types such as KrCl, KrBr, and ArF are contained as the luminescent gas 3G, the discharge does not start in the tube body 30 even when time elapses only by simply applying the voltage between the pair of electrodes (9 and 9). Therefore, the ultraviolet irradiation device 1 of this embodiment includes the start assist light source 5. The ultraviolet light L2 emitted from the start assist light source 5 is irradiated to the excimer lamp 3 in the lamp house 10 to facilitate the start of the discharge.

Especially, by setting the ultraviolet light L2 emitted from the start assist light source 5 to be the ultraviolet light belonging to the second wavelength band, the main emission wavelength of which is 250-300 nm, startability of the excimer lamp 3 is extremely improved. By irradiating the excimer lamp 3 with the ultraviolet light L2 belonging to the wavelength band while applying the voltage between the pair of electrodes (9 and 9), it is possible to light the excimer lamp 3 within one second, within a few seconds at the latest. This point is described with reference to a verification result.

Figure 5:
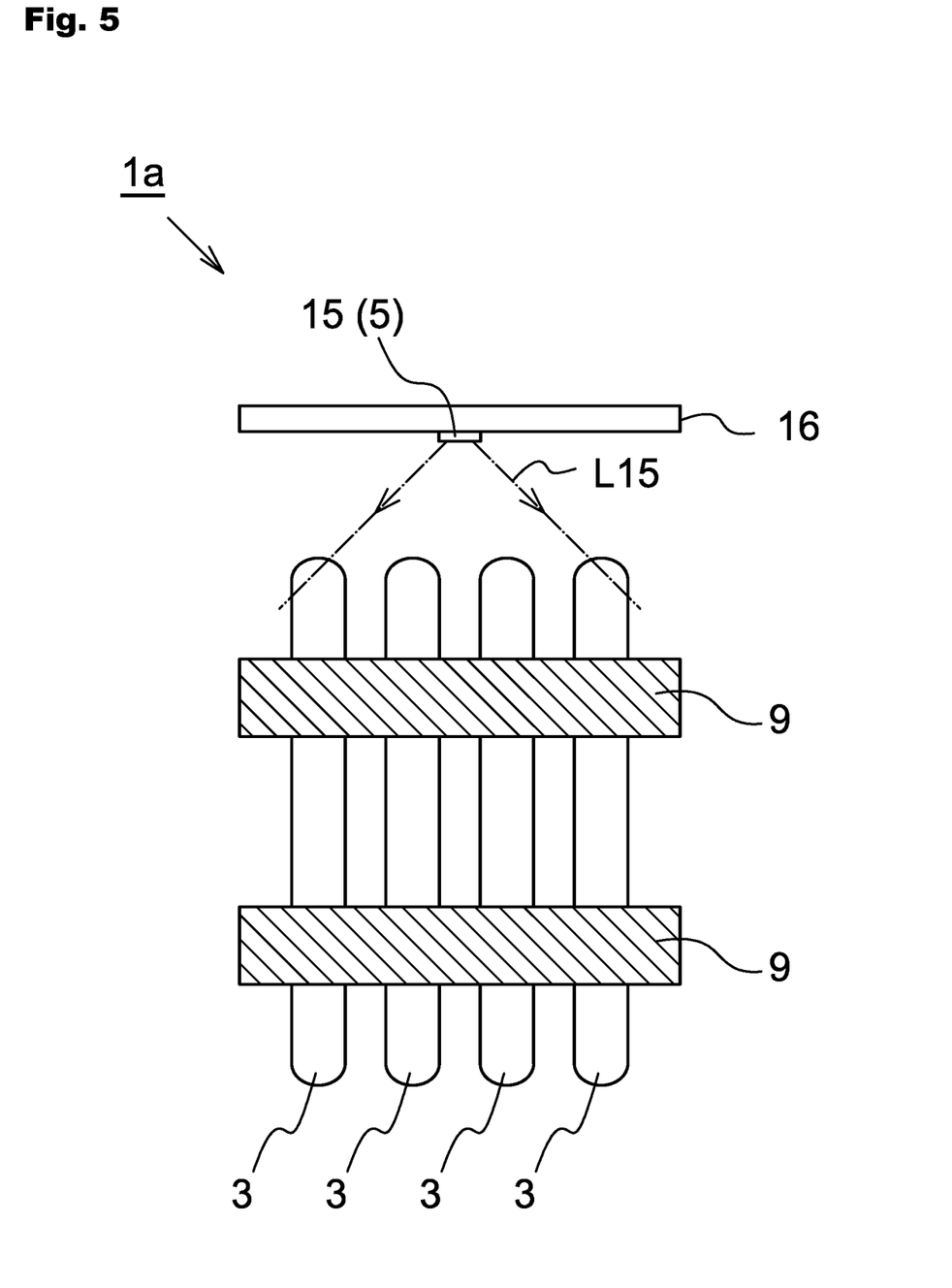
FIG. 5 is a view schematically illustrating a structure of an ultraviolet irradiation device used for verification.

FIG. 5 is a view schematically illustrating a configuration of a device for verification according to FIG. 2. An ultraviolet irradiation device 1a for verification is provided with four excimer lamps 3 described above, a pair of electrodes (9 and 9) for applying a voltage to each excimer lamp 3, and an LED light source 15 as the start assist light source 5. The LED light source 15 is mounted on an LED mounted board 16.

As the excimer lamp 3, the lamp in which the luminescent gas 3G containing krypton (Kr) and chlorine ($Cl_2$) is sealed was used. A sealing gas pressure at that time was set to 10 kPa.

As the LED light source 15, five types of light sources of different emission wavelengths were prepared.

A current of 20 mA was supplied to the LED light source 15 to emit light, and light from the LED light source 15 (LED light L15) was emitted toward the excimer lamp 3. In this state, by applying a high-frequency AC voltage of about 4 kV and 70 kHz to each excimer lamp 3, start-up delay time was measured. Note that, as a comparative example, similar verification was performed without lighting the LED light source 15. The result is illustrated in Table 1 below. Note that, in Table 1, the wavelength of the LED light L15 corresponds to a peak wavelength of the LED light L15 emitted from the LED light source 15.

TABLE 1

| Wavelength of LED Light L15 | Start-up Delay Time [Second] |
| --- | --- |
| None | Not Lit |
| White Light | Not Lit |
| 470 ± 5 nm | Not Lit |
| 405 nm | Not Lit |
| 365 nm | Not Lit |
| 280 nm | 0 |

According to the result in Table 1 above, in a case where the wavelength of the LED light L15 was set to 280 nm belonging to a UVC region, the excimer lamp 3 was lit immediately after the voltage application was started. In contrast, in a case where the LED light L15 was set to white light or in a case where the peak wavelength was set to 470±5 nm, 405 nm, and 365 nm, it was not possible to light the excimer lamp 3 even after an elapse of 60 seconds or longer after the voltage application was started as in the case where the LED light source 15 was not lit.

The present inventor deduces the reason for this as follows.

As described above, the luminescent gas 3G sealed in the excimer lamp 3 contains halogen such as chlorine. Halogen has a strong electron adhesion property and easily takes away electrons in the discharge space. Therefore, the excimer lamp 3 in which the luminescent gas 3G containing halogen is sealed tends to have poor startability. From such a point of view, it is considered that, if a halogen molecule (here, chlorine molecule) may be excited/dissociated, electrons in the discharge space are less likely to be taken away and the startability of the excimer lamp is improved.

From an energy level diagram of the chlorine molecules, excitation/dissociation energy of the chlorine molecules are assumed to be 4.1 eV or larger, which is 300 nm or shorter when converted into wavelength. Therefore, it is deduced that the startability of the excimer lamp 3 is significantly improved by irradiating the excimer lamp 3 with the LED light L15 from the LED light source 15 of the emission wavelength of 300 nm or shorter and photoexciting a chlorine gas contained in the luminescent gas 3G in the excimer lamp 3. That is, by irradiating the excimer lamp 3 with the ultraviolet light L2, the main emission wavelength of which belongs to the second wavelength band of 250-300 nm, the startability of the excimer lamp 3 may be improved.

In contrast, it is considered that, in a case where the LED light L15 is set to the white light or the peak wavelength of the LED light L15 is set to 470±5 nm, 405 nm, and 365 nm, the light energy entering the excimer lamp 3 does not reach the excitation/dissociation energy of the chlorine molecules, and an effect of improving the startability of the excimer lamp 3 cannot be obtained.

Figure 6:
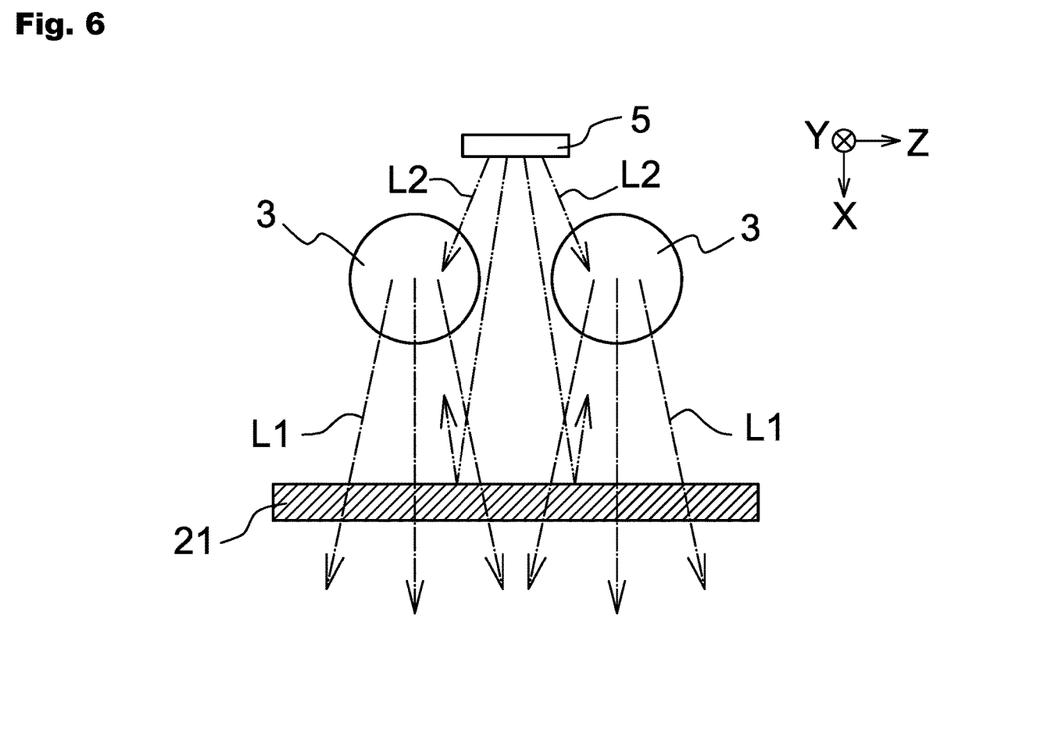
FIG. 6 is a view schematically illustrating a mode of travel of ultraviolet lights (L1 and L2) emitted from the excimer lamp and a start assist light source, respectively.

However, the ultraviolet light L2 belonging to the second wavelength band described above is considered to have an influence on a human body. From such a point of view, the ultraviolet irradiation device 1 is provided with the first optical filter 21 on the light extraction surface 10a in order to make it difficult for the ultraviolet light L2 to be emitted out of the lamp house 10. FIG. 6 is a view schematically illustrating a mode of travel of the ultraviolet lights (L1 and L2) emitted from the excimer lamp 3 and the start assist light source 5, respectively.

The first optical filter 21 has a characteristic of substantially transmitting the ultraviolet light L1 in the first wavelength band emitted from the excimer lamp 3, but substantially reflecting the ultraviolet light L2 in the second wavelength band emitted from the start assist light source 5. Such first optical filter 21 may be formed of a dielectric multilayer film composed of a plurality of materials having different refractive indices.

Figure 7:
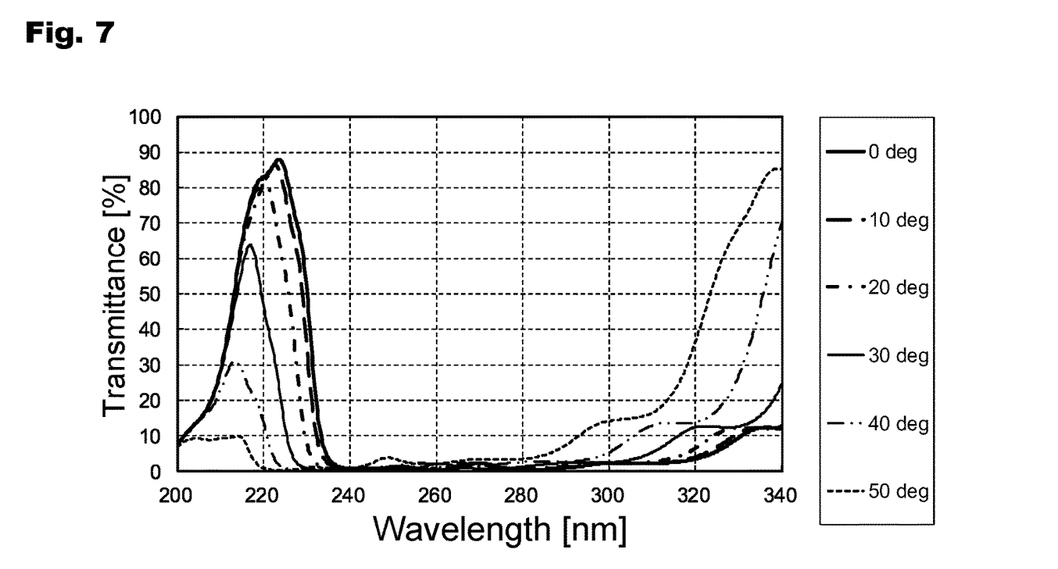
FIG. 7 is a graph illustrating an example of a transmission spectrum of a first optical filter.
Figure 8:
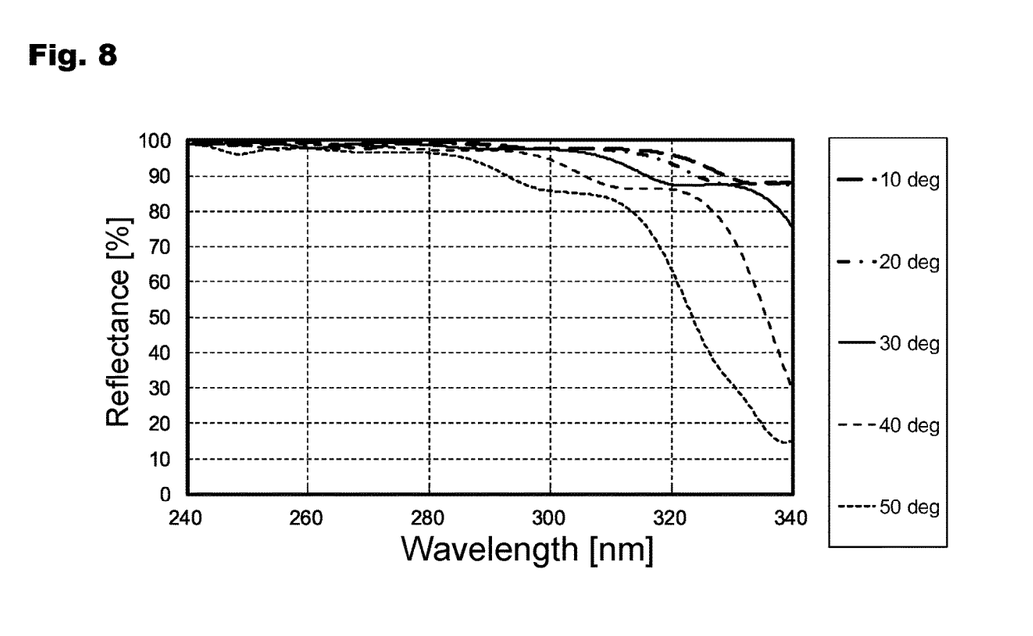
FIG. 8 is a graph illustrating an example of a reflection spectrum of the first optical filter.

FIG. 7 is a graph illustrating an example of a transmission spectrum of the first optical filter 21, and FIG. 8 is a graph illustrating an example of a reflection spectrum of the first optical filter 21. The graph in FIG. 7 is obtained by measuring a ratio of intensity of light emitted from the first optical filter 21 to intensity of light incident on the first optical filter 21 for each wavelength. Furthermore, the graph in FIG. 8 is obtained by measuring a ratio of the intensity of the light incident on the first optical filter 21 to intensity of light reflected by the first optical filter 21 for each wavelength.

Transmittance and reflectance of light of the first optical filter 21 formed of the dielectric multilayer film change depending on an incident angle of the light. Therefore, in FIGS. 7 and 8, the spectrum is illustrated for each incident angle of the light incident on the first optical filter 21. However, since a light emission unit and a light reception unit cannot be arranged on the same optical axis, data of a case where the incident angle is 0° is not illustrated in the graph in FIG. 8.

The first optical filter 21 having the characteristics illustrated in FIGS. 7 and 8 is designed assuming a case where the luminescent gas 3G of the excimer lamp 3 contains KrCl, that is, a case where the excimer lamp 3 emits the ultraviolet light L1, the main emission wavelength of which is 222 nm.

According to FIG. 7, the first optical filter 21 shows the transmittance of 60% or larger, more specifically about 80% or larger in a case where the ultraviolet light L1 of the wavelength of 222 nm is incident thereon at the incident angle of 20° or smaller. It is understood that even in a case of the incidence at the incident angle of 30° or smaller, the transmittance is about 40% or larger. Note that in a case where the main emission wavelength of the ultraviolet light L1 emitted from the excimer lamp 3 is 207 nm, it is sufficient to design to show the transmittance of 60% or larger with respect to the ultraviolet light L1 of the wavelength of 207 nm incident at the incident angle of 20° or smaller. Similarly, in a case where the main emission wavelength of the ultraviolet light L1 emitted from the excimer lamp 3 is 193 nm, it is sufficient to design to show the transmittance of 60% or larger with respect to the ultraviolet light L1 of the wavelength of 193 nm incident at the incident angle of 20° or smaller.

Furthermore, according to FIG. 8, it is understood that the first optical filter 21 shows the reflectance of 90% or larger, more specifically 95% or larger with respect to the ultraviolet light L2 belonging to the second wavelength band of 250-300 nm incident at the incident angle of 30° or smaller.

As schematically illustrated in FIG. 6, the ultraviolet light L2 belonging to the second wavelength band of 250-300 nm emitted from the start assist light source 5 is irradiated to the excimer lamp 3 to be used for assisting the start-up. Furthermore, when the ultraviolet light L2 traveling in the X direction is incident on the first optical filter 21 provided on the light extraction surface 10a side (refer to FIG. 1), most of the light is reflected by the first optical filter 21. As a result, the reflected light may also be used to assist the start-up of the excimer lamp 3 and is suppressed from being radiated out of the lamp house 10.

Furthermore, the excimer lamp 3 the discharge of which is started by lighting assistance by the ultraviolet light L2 emits the ultraviolet light L1 belonging to the first wavelength band of 190-230 nm. Since the first optical filter 21 shows high transmittance with respect to the ultraviolet light L1, when this is incident on the first optical filter 21 provided on the light extraction surface 10a side (refer to FIG. 1), this is directly transmitted through the first optical filter 21.

Therefore, according to the ultraviolet irradiation device 1, the ultraviolet light L1 belonging to the first wavelength band of 190-230 nm that is wanted to be used is radiated out of the lamp house 10 at high intensity, whereas the ultraviolet light L2 belonging to the second wavelength band of 250-300 nm having a risk of affecting the human body is suppressed from being radiated out of the lamp house 10.

Figure 9A:
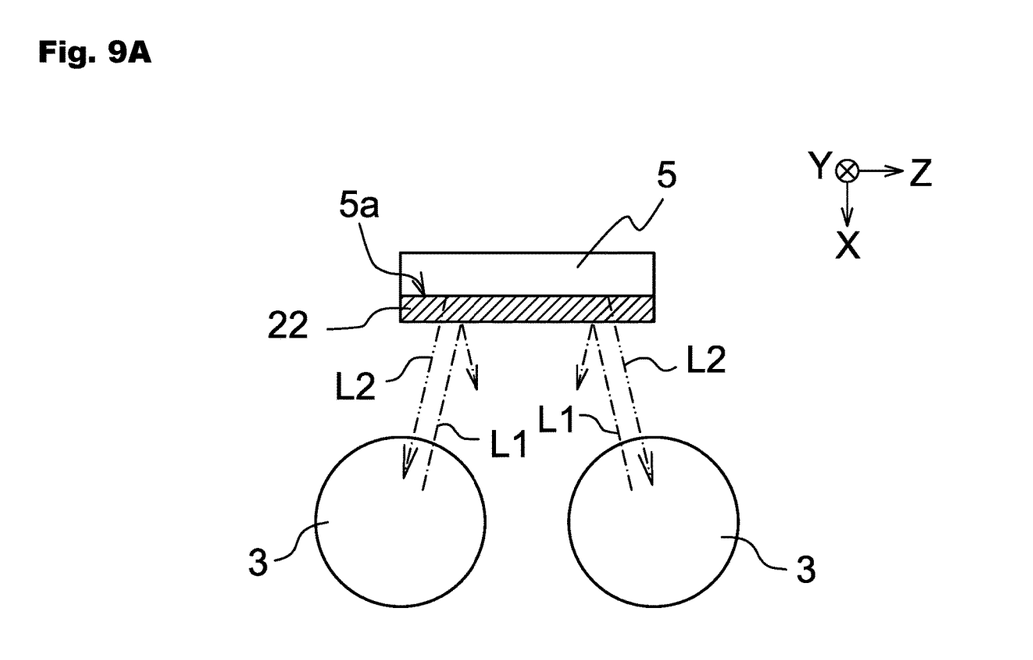
FIG. 9A is a view schematically illustrating a mode of travel of the ultraviolet lights (L1 and L2) emitted from the excimer lamp and the start assist light source, respectively.
Figure 9B:
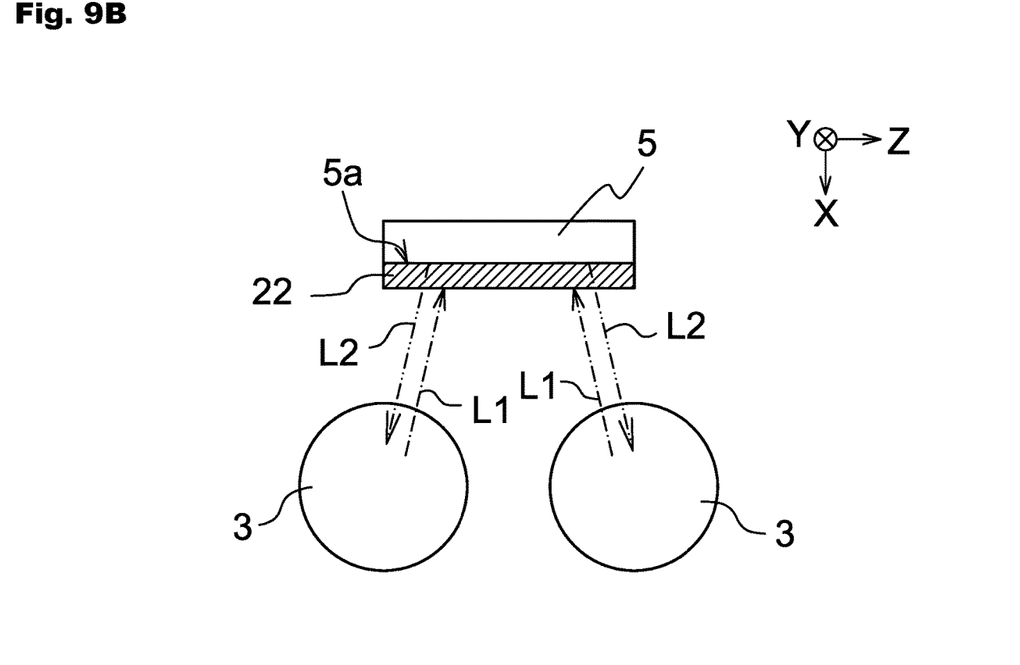
FIG. 9B is a view schematically illustrating another mode of travel of the ultraviolet lights (L1 and L2) emitted from the excimer lamp and the start assist light source, respectively.

Note that the ultraviolet irradiation device 1 of this embodiment may be provided with a second optical filter 22 that suppresses the transmission of the ultraviolet light L1 on a light emission surface 5a side of the start assist light source 5 (refer to FIGS. 9A and 9B). In an example illustrated in FIG. 9A, unlike the first optical filter 21, the second optical filter 22 is designed to substantially transmit the ultraviolet light L2 belonging to the second wavelength band, but substantially reflect the ultraviolet light L1 belonging to the first wavelength band. As is the case with the first optical filter 21, the second optical filter 22 is also formed of a dielectric multilayer film composed of a plurality of materials having different refractive indices.

As described above, the ultraviolet irradiation device 1 of this embodiment is provided with the start assist light source 5 in a position between the pair of electrodes (9 and 9) separated from each other in the Y direction as seen in the X direction. By arranging the start assist light source 5 in such a position, the ultraviolet light L2 emitted from the start assist light source 5 is likely to be irradiated to a region interposed between the pair of electrodes (9 and 9) of the excimer lamp 3, that is, the light emitting space. As a result, high startability of the excimer lamp 3 is obtained.

In contrast, after the lighting of the excimer lamp 3 is started, a part of the ultraviolet light L1 belonging to the first wavelength band of 190-230 nm travels to the start assist light source 5 side. In a case where the start assist light source 5 is the LED light source, an LED element is generally sealed with resin, so that the resin might be deteriorated over time due to the irradiation with the ultraviolet light L1.

However, as illustrated in FIG. 9A, since the start assist light source 5 includes the second optical filter 22 on the light emission surface 5a side, the ultraviolet light L1 emitted from the excimer lamp 3 to travel to the start assist light source 5 side may be reflected by the light emission surface 5a of the start assist light source 5. As a result, it is possible to inhibit the ultraviolet light L1 from being irradiated to the start assist light source 5, so that the deterioration in start assist light source 5 may be suppressed. Note that since the second optical filter 22 substantially transmits the ultraviolet light L2 in the second wavelength band emitted from the start assist light source 5, a function of assisting the start-up of the excimer lamp 3 is still secured.

Furthermore, since the second optical filter 22 provided on the light emission surface 5a of the start assist light source 5 reflects the ultraviolet light L1 in the first wavelength band emitted from the excimer lamp 3, a travel direction may be changed to the light extraction surface 10a side. As a result, the light intensity of the ultraviolet light L1 extracted from the ultraviolet irradiation device 1 is improved.

As another example, as illustrated in FIG. 9B, the second optical filter 22 may be designed to absorb the ultraviolet light L1 in the first wavelength band. In such a case also, it is possible to inhibit the ultraviolet light L1 from being irradiated to the start assist light source 5, so that the deterioration in start assist light source 5 may be suppressed. In this case also, since the second optical filter 22 substantially transmits the ultraviolet light L2 in the second wavelength band emitted from the start assist light source 5, the function of assisting the start-up of the excimer lamp 3 is still secured.

Note that a wall surface of the lamp house 10 and the electrodes (9 and 9) may also be formed of materials having high reflectance with respect to the ultraviolet light L1 in the first wavelength band. As an example, the wall surface of the lamp house 10 and the electrodes (9 and 9) may be made of metal or an alloy such as Al or stainless steel.

Second Embodiment

A second embodiment of an ultraviolet irradiation device according to the present invention is described mainly about a portion different from that of the first embodiment. Note that components common to those of the first embodiment are assigned with the same reference numerals and description thereof is omitted as appropriate.

Figure 10:
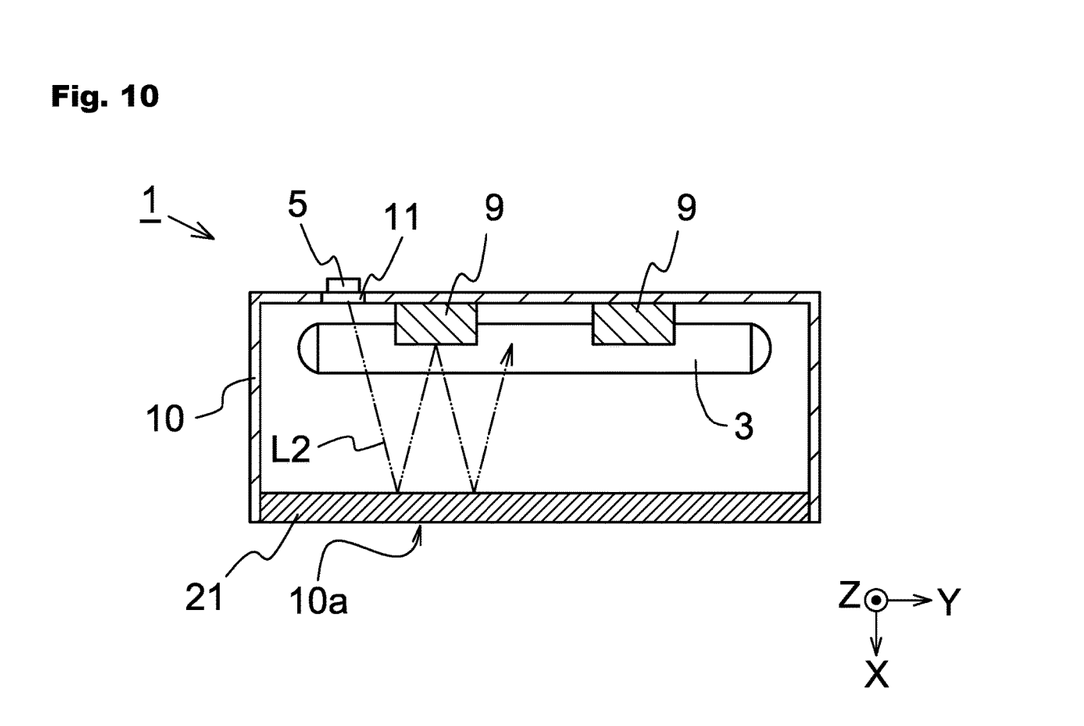
FIG. 10 is a cross-sectional view schematically illustrating a configuration of a second embodiment of an ultraviolet irradiation device of the present invention.

FIG. 10 is a cross-sectional view schematically illustrating an example of a configuration of the ultraviolet irradiation device of this embodiment. In the ultraviolet irradiation device 1 of the first embodiment, the start assist light source 5 is arranged in the position between the pair of electrodes (9 and 9) separated from each other in the Y direction as seen in the X direction. In contrast, this embodiment is different in that a start assist light source 5 is located outside a pair of electrodes (9 and 9) in the Y direction as seen in the X direction.

Even with such a configuration, a first optical filter 21 formed on a light extraction surface 10a has a characteristic of substantially reflecting ultraviolet light L2 in a second wavelength band emitted from the start assist light source 5, so that the ultraviolet light L2 may be guided into a light emitting space of an excimer lamp 3. As a result, startability of the excimer lamp 3 is improved. Furthermore, as in the first embodiment, by including the first optical filter 21, the ultraviolet light L2 in the second wavelength band being a wavelength band having a risk of affecting a human body is suppressed from being radiated out of a lamp house 10.

Furthermore, unlike the configuration of the first embodiment, in a case of this embodiment, the start assist light source 5 is arranged in a position away from a light emitting space of the excimer lamp 3. Therefore, as compared with the configuration of the first embodiment, ultraviolet light L1 in a first wavelength band emitted from the excimer lamp 3 after lighting is less likely to be irradiated to the start assist light source 5. Therefore, an effect that deterioration in start assist light source 5 is less likely to proceed may be obtained even if the second optical filter 22 as described above with reference to FIG. 9 is not provided on a light emission surface 5a of the start assist light source 5.

Note that although FIG. 10 illustrates a case where the ultraviolet light L2 is reflected by the first optical filter 21 and the electrode 9 and then guided into the light emitting space of the excimer lamp 3, the ultraviolet light L2 may be directly irradiated into the light emitting space of the excimer lamp 3 from the start assist light source 5, or the ultraviolet light L2 may be irradiated into the light emitting space of the excimer lamp 3 after being reflected once by the first optical filter 21.

Figure 11:
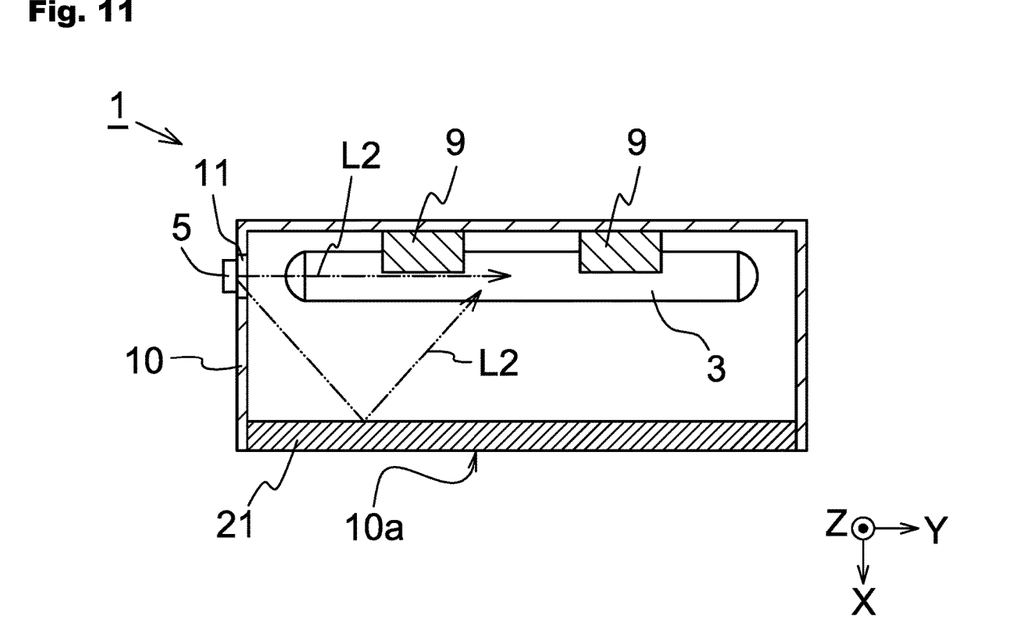
FIG. 11 is a cross-sectional view schematically illustrating the configuration of the second embodiment of the ultraviolet irradiation device of the present invention.

FIG. 11 is a cross-sectional view schematically illustrating another example of the configuration of the ultraviolet irradiation device of this embodiment. As illustrated in FIG. 11, by arranging the start assist light source 5 in the same position as the position in which the excimer lamp 3 is arranged in the X direction, the ultraviolet light L2 emitted from the start assist light source 5 is easily directly guided into the light emitting space of the excimer lamp 3. Furthermore, the ultraviolet light L2 in the second wavelength band that travels from the start assist light source 5 to the light extraction surface 10a side is reflected by the first optical filter 21, so that it may be guided into the light emitting space of the excimer lamp 3 and is suppressed from being radiated out of the lamp house 10.

Figure 12:
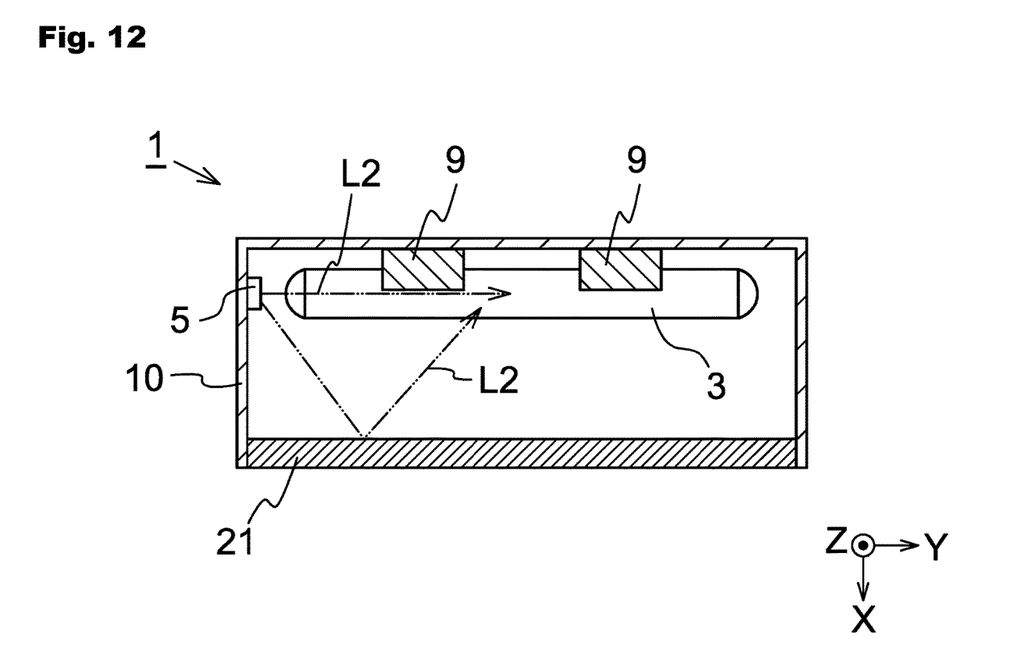
FIG. 12 is a cross-sectional view schematically illustrating the configuration of the second embodiment of the ultraviolet irradiation device of the present invention.

Moreover, as illustrated in FIG. 12, the start assist light source 5 may also be arranged in the lamp house 10. In an example illustrated in FIG. 12, the start assist light source 5 is fixed to an inner wall of the lamp house 10. Note that, in the configuration illustrated in FIG. 10 and the configuration illustrated in FIG. 11 also, the start assist light source 5 may be similarly arranged in the lamp house 10.

Another Embodiment

Hereinafter, another embodiment is described.

<1> In each embodiment described above, the case where the start assist light source 5 is the LED light source is described. However, the start assist light source 5 is any light source as long as this is the light source that emits the ultraviolet light L2, the main emission wavelength of which belongs to the second wavelength band of 250-300 nm, and has faster startability than that of the excimer lamp 3. As an example other than the LED light source, the start assist light source 5 may be formed of a low-pressure mercury lamp.

<2> The configuration of the excimer lamp 3 described above with reference to FIG. 3 is merely an example. A structure of the excimer lamp 3 is any structure as long as the lamp emits the ultraviolet light L1, the main emission wavelength of which belongs to the first wavelength band of 190-230 nm. As an example, the excimer lamp 3 may have a structure in which two tube bodies are provided concentrically and the luminescent gas 3G is sealed between an inner tube and an outer tube (double tube structure). Furthermore, as another example, the excimer lamp 3 may have a structure (single tube structure) in which electrodes are provided inside and outside a single tube body in which the luminescent gas 3G is sealed, or a structure (flat tube structure) in which electrodes are provided on two surfaces facing each other of a tube body having a rectangular surface in which the luminescent gas 3G is sealed.

<3> In the above-described embodiment, the case where the first optical filter 21 is provided on the light extraction surface 10a of the lamp house 10 is described. However, a place in which the first optical filter 21 is provided is not limited to the light extraction surface 10a, and a similar effect is obtained when this is provided in a place through which the ultraviolet light L1 emitted from the excimer lamp 3 pass in the lamp house 10.

<4> In the above-described embodiment, the case where the ultraviolet irradiation device 1 is provided with the first optical filter 21 is described. However, in a case where there is a circumstance that the ultraviolet light in the second wavelength band emitted from the start assist light source 5 is allowed to be radiated in an irradiation space such as in a case where the ultraviolet irradiation device 1 is operated only in a case where no human being is present in the same space, for example, the ultraviolet irradiation device 1 is not necessarily provided with the first optical filter 21.

DESCRIPTION OF REFERENCE SIGNS

1 Ultraviolet irradiation device
1a Ultraviolet irradiation device for verification
3 Excimer lamp
3G Luminescent gas
5 Start assist light source
5a Light emission surface of start assist light source
9 Electrode
10 Lamp house
10a Light extraction surface
11 Light transmissive window
15 LED light source
16 LED mounted board
21 First optical filter
22 Second optical filter
30 Tube body

The invention claimed is:
1. An ultraviolet irradiation device comprising:
a lamp house on at least one surface of which a light extraction surface is formed;
an excimer lamp accommodated in the lamp house, the excimer lamp that emits ultraviolet light, a main emission wavelength of which belongs to a first wavelength band of 190-230 nm;
a start assist light source arranged in a position in which ultraviolet light, a main emission wavelength of which belongs to a second wavelength band of 250-300 nm, is capable of being irradiated to the excimer lamp; and
a first optical filter that substantially transmits the ultraviolet light in the first wavelength band and substantially reflects the ultraviolet light in the second wavelength band, the first optical filter being arranged in the lamp house at a place that the ultraviolet light radiated from the excimer lamp passes through.

2. The ultraviolet irradiation device according to claim 1, wherein
the first optical filter is arranged on the light extraction surface of the lamp house.

3. The ultraviolet irradiation device according to claim 1, wherein
a luminescent gas containing KrCl or KrBr is sealed in the excimer lamp.

4. The ultraviolet irradiation device according to claim 1, wherein
the start assist light source is an LED light source including a light emission surface that emits the ultraviolet light in the second wavelength band.

5. The ultraviolet irradiation device according to claim 4, wherein
the excimer lamp includes a pair of electrodes formed on an outer wall of a tube body forming the excimer lamp and arranged apart from each other in a tube axis direction of the tube body,
the start assist light source includes a second optical filter arranged on the light emission surface that substantially transmits the ultraviolet light in the second wavelength band and substantially inhibits the ultraviolet light in the first wavelength band from being irradiated to the start assist light source, and
the start assist light source is arranged in a position between the pair of electrodes in the tube axis direction as seen in a direction orthogonal to the light extraction surface.

6. The ultraviolet irradiation device according to claim 4, wherein
the excimer lamp includes a pair of electrodes formed on an outer wall of a tube body forming the excimer lamp and arranged apart from each other in a tube axis direction of the tube body, and
the start assist light source is arranged in a position outside the pair of electrodes in the tube axis direction as seen in a direction orthogonal to the light extraction surface.

7. The ultraviolet irradiation device according to claim 6, wherein
the lamp house is such that an inner wall of at least one surface other than the light extraction surface is formed of a material that substantially reflects the ultraviolet light in the second wavelength band.

8. The ultraviolet irradiation device according to claim 4, further comprising
a light transmissive window provided on a part of a wall surface of the lamp house, wherein
the start assist light source is arranged so as to be fixed to the wall surface of the lamp house outside the lamp house in a state in which the light emission surface faces the light transmissive window.

9. The ultraviolet irradiation device according to claim 2, wherein a luminescent gas containing KrCl or KrBr is sealed in the excimer lamp.

10. The ultraviolet irradiation device according to claim 2, wherein the start assist light source is an LED light source including a light emission surface that emits the ultraviolet light in the second wavelength band.

11. The ultraviolet irradiation device according to claim 3, wherein the start assist light source is an LED light source including a light emission surface that emits the ultraviolet light in the second wavelength band.

12. The ultraviolet irradiation device according to claim 9, wherein the start assist light source is an LED light source including a light emission surface that emits the ultraviolet light in the second wavelength band.

* * * * *